United States Patent
Fan et al.

(10) Patent No.: US 7,536,043 B2
(45) Date of Patent: May 19, 2009

(54) FLOW REPRESENTATION METHOD AND SYSTEM FOR MEDICAL IMAGING

(75) Inventors: Liexiang Fan, Issaquah, WA (US); Wayne J. Gueck, Redmond, WA (US); King Yuen Wong, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 760 days.

(21) Appl. No.: 10/642,914

(22) Filed: Aug. 18, 2003

(65) Prior Publication Data

US 2005/0041837 A1  Feb. 24, 2005

(51) Int. Cl.
G06K 9/00 (2006.01)
A61B 8/00 (2006.01)
G01F 1/00 (2006.01)

(52) U.S. Cl. ............... 382/128; 600/454; 600/504; 73/861

(58) Field of Classification Search .......... None
See application file for complete search history.

(56) References Cited

U.S. PATENT DOCUMENTS

| | | | |
|---|---|---|---|
| 4,573,477 A | 3/1986 | Namekawa et al. | |
| 4,622,977 A | 11/1986 | Namekawa et al. | |
| 4,641,668 A | 2/1987 | Namekawa | |
| 4,785,402 A | 11/1988 | Matsuo et al. | |
| 4,911,171 A | 3/1990 | Uehibori | |
| 5,105,817 A | 4/1992 | Uehibori et al. | |
| 5,224,482 A | 7/1993 | Nikoonahad | |
| 5,231,573 A | 7/1993 | Takamizawa | |
| 5,622,174 A | 4/1997 | Yamazaki | |
| 5,632,277 A | 5/1997 | Chapman et al. | |
| 5,677,501 A * | 10/1997 | Kawaguchi et al. | 73/866.3 |
| 5,706,819 A | 1/1998 | Hwang et al. | |
| 6,280,387 B1 | 8/2001 | Deforge et al. | |
| 6,542,153 B1 | 4/2003 | Liu et al. | |
| 6,632,177 B1 | 10/2003 | Phillips | |
| 6,733,455 B2 * | 5/2004 | Mo et al. | 600/454 |

FOREIGN PATENT DOCUMENTS

JP  02-161934  * 6/1990

(Continued)

OTHER PUBLICATIONS

"Detecting Blood Reflectors," dated 1997.

(Continued)

*Primary Examiner*—Charles Kim

(57) ABSTRACT

Flow is represented by a synthesized or artificial pattern. Motion is visualized by apparent displacement of pixels from one frame to the next. An artificial pattern is introduced in order to present the flow. A changing parameter, such as velocity, is viewed as a function of multiple images or over time. The rate of change of the parameter is proportional to the perceived or actual motion. Humans perceive flow as a live stream, such as tap water pouring from a faucet or a stream in a creek. Flow associated with medical imaging is presented in a similar way, such that a pattern or other flow information persists over multiple images. The flow is synthesized by generating patterns and moving the generated patterns in the field of view. The direction and rate of motion of the pattern are a function of the direction and rate of the flow.

15 Claims, 2 Drawing Sheets

FOREIGN PATENT DOCUMENTS

JP    10-94519    *    4/1998

OTHER PUBLICATIONS

"How B-Flow Images are Formed," dated 1995.

"Ultrasound Technical Tutorial—B-Flow," GE Medical Systems; http:www.gemedicalsystems.com/rad/us/eduction/msutut4htm.; printed Sep. 18, 2003.

"Advances in B-Mode Imaging—Photopic and SieFlow Ultrasound," by E. Sauerbrei, L. Nazaraian, C. Douville, R. Haerten, R. Ingham and V. Norka; Electormedica 68 (2000) No. 2, pp. 127-134.

* cited by examiner

FLOW REPRESENTATION METHOD AND SYSTEM FOR MEDICAL IMAGING

BACKGROUND

The present invention relates to imaging flow. In particular, magnitude and directional flow information is provided.

In medical diagnostic ultrasound, power mode, color Doppler mode or spectral Doppler mode is used to detect flow information in a region being imaged. One or both of velocity and energy associated with the flow are estimated and used to display flow information. For example, color Doppler velocity detects both a direction of flow relative to the transducer (e.g., flow towards and flow away from the transducer) as well as the velocity or speed of the flow. For any single image, the color for spatial locations associated with flow is modulated as a function of the direction and magnitude of the velocity. For example, a red indicates flow towards a transducer and blue indicates flow away from the transducer, and the brightness of the blue or red color indicates the magnitude of the flow. Any single image presents the detected information to the user. However, the perception of flow through a sequence of images is negligible. For two- or three-dimensional imaging, the direction of flow being towards or away from the transducer provides even more limited directional information.

In an effort to provide further directional information, a two-dimensional directional vector is determined. For example, speckle is tracked from one frame of data to another frame of data. By determining a correlation in the speckle at translated positions between images, the two-dimensional direction of flow is determined. To communicate the flow information for a given image, a color wheel is used. Different colors are provided around the circumference of the wheel to represent flow in different directions. The magnitude or speed of the flow is calculated using the speckle correlation or angle corrected velocity information. Greater magnitudes are associated with brighter presentations of the color representing direction. Any single image presents the flow information to a user when displayed alone. However, the perception of flow through a sequence of images is negligible. The colors for subsequent images may or may not vary in brightness or hue from previous images, resulting in no perception of flow through a sequence of images. Due to the many colors in each image to depict the flow, the images are perceptually busy or disclose sufficient amounts of information that a user has trouble conceptualizing and using all of the information.

BRIEF SUMMARY

The present invention is defined by the following claims, and nothing in this section should be taken as a limitation on those claims. By way of introduction, the preferred embodiments described below include medical diagnostic methods and systems for representing flow. Motion is visualized by apparent displacement of pixels from one frame to the next. An artificial pattern is introduced in order to present the flow. A changing parameter, such as velocity, is viewed as a function of multiple images or over time. The rate of change of the parameter is proportional to the perceived or actual motion. Humans perceive flow as a live stream, such as tap water pouring from a faucet or a stream in a creek. Flow associated with medical imaging is presented in a similar way, such that a pattern or other flow information persists over multiple images. The flow is synthesized by generating patterns and moving the generated patterns in the field of view. The direction and rate of motion of the pattern are a function of the direction and rate of the flow.

In a first aspect, a method for presenting flow with a medical imaging system is provided. A rate of change of a display parameter is determined as a function of a perceived motion of a pixel. A change in the parameter is displayed over time as a function of the rate of change.

In a second aspect, a method for representing flow with the medical imaging system is provided. Display values for each of a first plurality of spatial locations are assigned. The flow direction and magnitude are tracked for each of the first plurality of spatial locations. A second plurality of spatial locations is identified as a function of the flow directions and magnitudes. Display values for each of the second plurality of spatial locations are assigned as a function of the first display values.

In a third aspect, a method for representing flow with a medical imaging system is provided. A first pattern is generated for a plurality of pixels associated with flow for a first image. A second pattern is generated for pixels associated with flow for a second image. The second pattern is responsive to the first pattern.

In a fourth aspect, a system for representing flow in medical imaging is provided. A processor is operable to generate and at least partially persist a pattern in each of at least two images. The persistent pattern shifts as a function of at least one of flow direction, flow magnitude and combinations thereof. A display is operable to display the images.

Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Flow is presented as a pattern that persists between sequential images. Two- or three-dimensional images are displayed as a function of time (e.g., 3-D imaging over time is 4-D imaging). To allow more instinctive visualization of flow, the pattern or a variation of the pattern is repeated in subsequent images. The generated pattern is moved according to the attributes of the flow. The pattern is shifted or changed as a function of flow, variance or rate of change in the parameter being represented, such as velocity. As a result, flow is viewed in a sequence of images. Since the patterns are generated for sensing motion and may not correspond to stationary or non-stationary contexts of any given individual image, a live stream is presented. If a single image is displayed alone, the stationary context of the image is provided and a pattern representing the non-stationary context may still demonstrate some aspect of motion but may not provide a perception of motion. As the flow parameter changes over time, the pattern is also changed. The pattern is artificial so it does not rely on observed objects such as blood cells.

Figure 1:
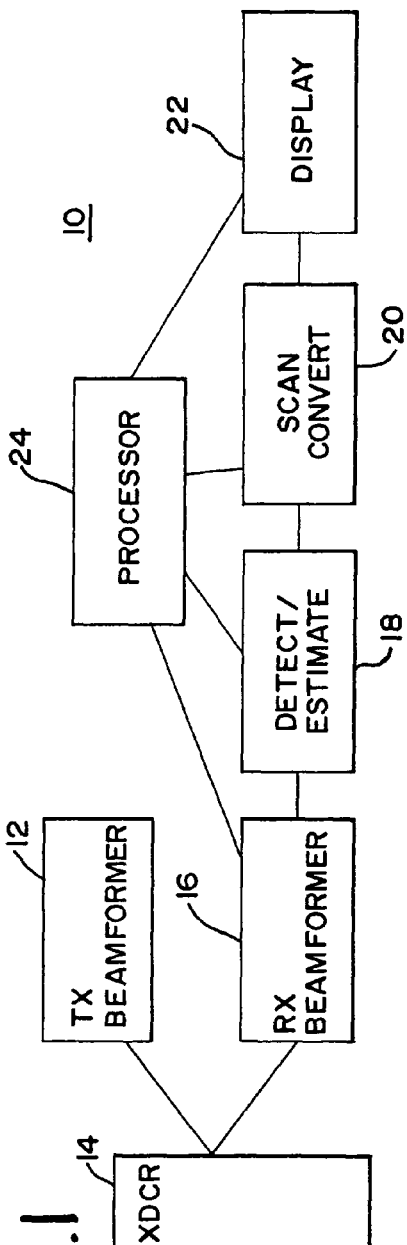
FIG. 1 is a block diagram of a medical diagnostic ultrasound system for flow representation in one embodiment.

FIG. 1 shows a system 10 for representing flow in medical imaging. The system 10 includes a transmit beamformer 12, a transducer 14, a receive beamformer 16, a detector 18, a scan converter 20, a display 22 and a processor 24. Additional different or fewer components may be provided. For example, the system 10 includes the processor 24 and the display 22 as a workstation independent of the acquisition of ultrasound data. The embodiments discussed herein relate to ultrasound, but flow may be represented for other medical imaging modalities, such as x-ray, MRI, computed tomography or other now known or later developed systems.

The transmit beamformer 12 includes a plurality of waveform generators for generating waveforms for one or more elements of the transducer 14. The transducer 14 converts the electrical waveforms from the transmit beamformer 12 into acoustic energy. Using phased array techniques or relative delays and apodization of the transmit waveforms, the transducer 12 focuses acoustic energy along one or more scan lines. Echoes responsive to the transmitted acoustic energy are received by the transducer 14. The transducer 14 converts the acoustic echoes into electrical signals. The electrical signals are provided to the receive beamformer 16. The receive beamformer 16 processes the signals from each of the elements in a receive aperture by applying relative delays and apodization. The signals are then summed to provide a representation of one or more spatial locations of the patient.

The detector 18 determines intensity, magnitude, energy, velocity, variance or combinations thereof from the received beamformed data. In one embodiment, the detector 18 is a Doppler or flow estimator for estimating velocity, energy and/or variance. In another embodiment, the detector 18 is a B-mode processor for detecting the intensity of the envelope of the received signal. Other now known or later developed detectors or estimators may be used. For two-dimensional imaging, the scan and associated detection provides estimates or ultrasound values for each of a plurality of spatial locations in a two-dimensional region of the patient. For three-dimensional imaging, values are provided for various spatial locations within a three-dimensional volume.

The detected information is provided to a scan converter 20. The scan converter 20 converts the detected information from an acquisition domain to a display domain, such as converting from a polar coordinate format to a Cartesian coordinate format. The scan converted information is then presented on the display 22. In one embodiment for representing flow, a given image includes B-mode information associated with stationary or substantially stationary tissue. One or more additional regions of the image are associated with flow. For pixels or spatial locations associated with flow, the display values are generated, at least in part, by the processor 24.

The processor 24 is a control processor, general processor, application specific integrated circuit, digital signal processor, analog component, digital component, memory device, combinations thereof or other now known or later developed device for persisting a pattern to represent flow. In one embodiment, the processor 24 is an overall or system processor. In alternate embodiments, the processor 24 is a processor within either of the control path of one or more components of the system 10 or a processor within the ultrasound data path of the system 10. In one embodiment, the processor 24 is a processor within the detector 18. A plurality of different processors may be used to implement different functions of the processor 24 described herein in a sequential or parallel fashion.

The processor 24 is operable to generate an at least partially persistent pattern in each of at least two images. The persistent pattern is shifted in one image relative to another image as a function of a direction of flow, a magnitude of flow, energy of flow, variance of flow or a combination thereof. As a result, the user perceives flow as a function of time. To generate the persistent pattern, the processor 24 is operable to assign a pattern to a plurality of spatial locations or pixels in one image. The flow direction and magnitude for each of the spatial locations is then tracked. Spatial locations association with the flow direction and magnitude are then identified, such as spatial locations offset in the tracked direction and at a distance corresponding to the tracked magnitude. A pattern is then generated for the identified spatial locations in a subsequent image. The display values assigned to the identified spatial locations in the subsequent image are assigned as a function of the display values for the different spatial locations in the previous image. The pattern of display values from the previous image is, at least in part, persisted to different spatial locations in a subsequent image.

The display 22 displays an image responsive to the pattern or display values assigned by the processor 24. Where a sequence of images is shown as a function of time, the user perceives a pattern moving in the flow direction and with the flow magnitude across the images. The pattern may be altered as a function of changes in the flow, but generally or perceptually persists from one image to the next.

Figure 2:
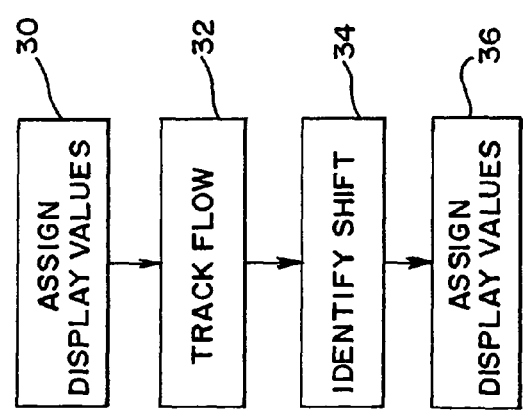
FIG. 2 is a flow diagram of one embodiment of a method for flow representation.

FIG. 2 shows one embodiment of a method for representing flow with a medical imaging system. Additional, different or fewer acts than shown in FIG. 2 may be provided. In general, the process of FIG. 2 determines a display parameter, namely the rate of change of position. In general, the parameter displayed is a time variation of an associated parameter. For example, the velocity, acceleration, elasticity or combinations thereof associated with flowing fluid or moving tissue is monitored for a change over time. In FIG. 2, the rate of change, flow, is displayed as displacement proportional to flow. Velocity is represented by motion in one embodiment. The flow direction and magnitude determine the spatial location of the displaced image pixel. The rate of change is a function of the flow direction and magnitude. Other flow characteristics than velocity may be used. For example, the acceleration is the rate of change of velocity over time. A change in the velocity parameter is then displayed over time as a displacement of an image pixel representing the velocity at that point. A pattern over a plurality of pixel locations is displayed where the pattern varies as a function of the rate of change. In this manner, any time variation of a parameter that is directionally oriented can be displayed in this manner; simply take the pixel representing the parameter and displace it in the direction oriented by an amount determined by the variation.

In the velocity flow example above, the position of the pattern from one image to another image changes as a function of the flow direction and magnitude. For example, the overall pattern is shifted by an overall flow direction and magnitude. Alternatively, the display values for individual pixels making up the pattern are shifted as a function of the flow direction and magnitude associated with each of the pixels in subsequent images. While the pattern may vary as a function of different flow directions and magnitudes, the pattern is perceived as persisting, representing flow over time.

For a non-medical analogy, humans perceive flow through a shallow stream bed as varying across the width of the stream bed yet having patterns that continue over time (i.e., the flow is perceived over time as moving, despite some changes or differences in movement for different locations).

Figure 3:
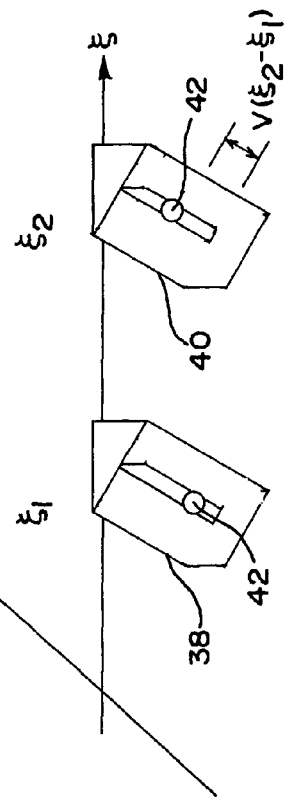
FIG. 3 is a graphical representation of one embodiment of separation of acquisition time from display time for persisted display of a flow representation.

The flow is represented as function of time. The acquisition time may be different than the display time, so the flow is presented as a function of the display time. A plurality of images are acquired as a function of acquisition time. The set of images is represented by I(x, y, t) where x and y are spatial dimensions and t is the time of acquisition. For 4-D imaging, the set of images is represented by I(x, y, z, t) where x, y, and z are spatial dimensions and t is the time of acquisition. This image information includes one or more components, such as a changing parameter and a static parameter. For example, in 2-D image sequences over time, one component is velocity information represented by: v(x, y, t) and another component is static B-mode information represented by s(x, y, t). Both B-mode and color flow information are provided for each acquisition time. Since acquired images may be stored, such as in a CINE memory or CINE loop format, the display time may be different than in acquisition time. FIG. 3 shows a representation of the relationship between acquisition time and display time. The acquisition time axis is shown as t. Each acquired two- or three-dimensional image is associated with a time of acquisition. The first acquisition begins at time 0 and subsequent acquisitions are at times later than time 0. Since any arbitrary image may be selected for an initial display from memory, the start of the display time, ξ is arbitrary. Where pattern generation and display time is performed in real time with acquisition, the time axis t and the display axis ξ are a same axis or direction. When observing a static image, the display axis ξ is perpendicular to the acquisition time axis t. The persistent pattern discussed herein changes as a function of display time. The pattern is independent of the acquisition time. Any beginning image in the display time is associated with a pattern that is independent of previously acquired images. The pattern is then persisted as a function of changes in the display time between images. An angle between the acquisition time and the display time axes is a function of the frame rates of the acquisition time and the display time. Where the frame rates are equal, such as in real time imaging, the angle is 0. Where the frame rates are not equal, the angle between the axes increases. By representing flow as a function of the display time, an artificial pattern is used independent of the location of a beginning image in a sequence within the sequence.

The artificial pattern represented by a circle 42 in FIG. 3 is generated and moved in the display time axis as shown in the images 38 and 40. The pattern is moved as a function of the display time rather than the acquisition time. As a result, the rate of change of a parameter, such as the velocity magnitude, is determined between sequential images in display time. The velocity magnitude of interest is the velocity between two images as a function of the frame rate as displayed. For example, the pattern 42 is shown as shifted by a velocity magnitude as a function of the difference of the display times associated with the images 38 and 40. Alternatively, the shift is a function of the acquisition time.

Referring again to FIG. 2, display values are assigned in act 30. Display values are assigned to a plurality of spatial locations or pixels in a first image. Image includes an actual displayed image as well as a frame of data eventually displayed as an image. The plurality of spatial locations or pixels in the image for assigning display values is identified as locations associated with flow. Any of various now known or later developed methods may be used for identifying locations associated with flow. In one embodiment, sufficiently high flow energy or velocity values indicate the existence of flow. Other processes used for determining where to display flow mode information as opposed to B-mode information may be used.

Figure 4:
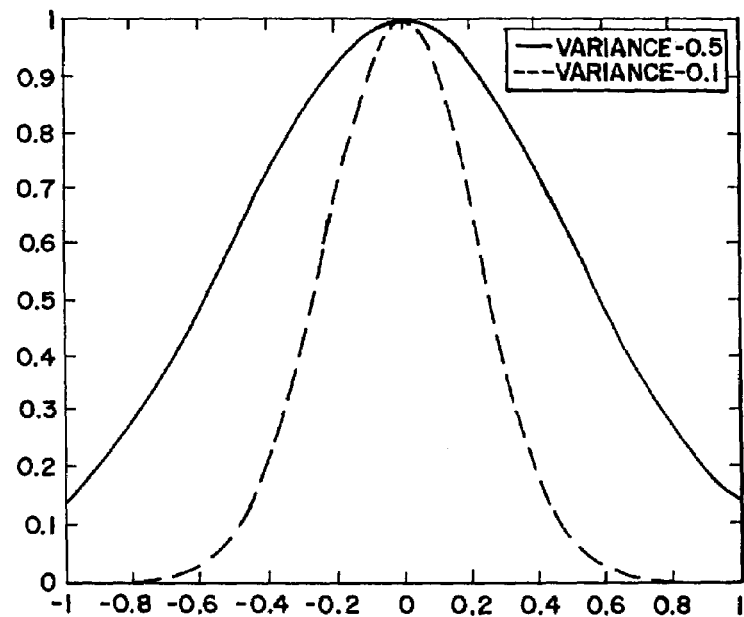
FIG. 4 is a graphical representation of a distribution of a pattern in one embodiment.

The display values for the locations associated with flow are assigned as a function of a pattern. The pattern, represented by p(x, y, ξ), is arbitrary. It may be based on ultrasound data or it may be randomly generated. The pattern is a function of the echo magnitude in one embodiment. In one embodiment, a random field pattern with a normal distribution is generated. FIG. 4 shows two normal distributions associated with random patterns. The width of the distribution is controlled by ultrasound data in one embodiment. For example, the variance of flow associated with a region, all spatial locations associated with flow, a maximum flow spatial location, a minimum flow spatial location or other single or group spatial locations is determined. The distribution of the random pattern is set as a function of the variance. A small variance has a lesser width, resulting in a pattern with a preponderance of pixels dominated by one value, as shown by the dashed line in FIG. 4. A greater variance provides a wider distribution in the random pattern, resulting in greater variance within the pattern. As an alternative or additional embodiment, the magnitude of the echo information, such as either B-mode or flow energy, is used to control the distribution of the pattern. While the random field with a Gaussian shape is shown for one embodiment of the pattern, other set or variable patterns may be used. An experimentally designed pattern, a pattern calculated as a function of any of various parameters, a pseudorandom pattern, non-random or other patterns may be used.

The pattern is used to assign at least one characteristic or component of pixel display values. For example, a gray scale level, a color, hue, brightness or combinations thereof are modulated as a function of the pattern. For example, a gray scale level of each spatial location or pixel associated with flow is assigned as a function of the pattern. The pattern is distributed across the plurality of spatial locations. Using the random pattern discussed above, a speckular appearing pattern is generated for a given image across all or a subset of spatial locations associated with flow.

The display values for pixels or locations associated with this flow are modulated as a function of additional signals in one embodiment. For example, B-mode information associated with each of the spatial locations is also used to modulate gray scale values. Since B-mode signals are more static than flow, as the pattern shifts in subsequent images, the B-mode information is maintained substantially stationary or relatively stationary. As another example, the color hue and/or brightness for each spatial location is modulated as a function of color flow signals. The velocity, energy, variance or combinations thereof associated with each spatial location modulates the color, such as used in color Doppler velocity and color Doppler energy imaging. As a result, a given image includes one or both B-mode and color or flow mode information for spatial locations associated with flow as well as the pattern information generated to represent flow over time. In alternative embodiments, the spatial locations associated with flow are modulated only in response to the pattern for representing flow over time.

In act 32, the flow direction and magnitude are tracked for each of the plurality of spatial locations associated with flow. Alternatively, only one of flow direction or magnitude is tracked. Other flow characteristics may alternatively or additionally be tracked. Any now known or later developed method for tracking flow is used. In one embodiment, flow direction and magnitude are tracked as velocity information. The direction is one of towards or away from the transducer 14. The magnitude is associated with the speed towards or away from the transducer. Alternatively, a two-dimensional or three-dimensional flow direction is tracked. For example, a correlation between speckle patterns in two different images is used to indicate a direction and magnitude of flow. By taking a speckle region of one image and searching for a location of highest correlation in a subsequent image, a flow direction and magnitude are identified. Flow direction may be identified using speckle tracking and the magnitude determined from angle corrected Doppler velocity information.

In another embodiment, the two-dimensional velocity vector is calculated by modulating the transmitted beam of acoustic energy. The received signals are analyzed to determine a left or right shift in phase of the amplitude. The amount of shift indicates a lateral component or component parallel to the face of the transducer. Using the Doppler velocity or other velocity representing the movement to and away from the transducer, the two-dimensional direction is determined. The magnitude of the change is provided either by the phase shift or by angle correcting the Doppler velocity.

In yet another embodiment, flow direction and magnitude are tracked as a function of user input. The user inputs a direction of flow. The magnitude of the flow is then determined by angle correcting velocity information. In yet another alternative embodiment, the direction of flow is determined based on the shape of a region of spatial locations associated with flow. Where a vessel is being imaged, a single elongated shape is provided in each image. Where the vessel is not parallel to the face of the transducer, the direction of flow within the vessel is determined by the orientation of the vessel. Using the orientation of the elongated vessel, the magnitude information may also be angle corrected.

In act 34, spatial locations are identified in a subsequent image. The spatial locations are identified as a function of the flow direction and magnitude or other flow characteristic. For example, a flow direction and magnitude for a given pixel in the first image represented by x1, y1 indicates movement of the pixel to a different location x2, y2 by the subsequent image in display time. Given the magnitude and direction of velocity, each of the plurality of spatial locations in a first image associated with flow move to other spatial locations in a subsequent image. In one embodiment, the movement for each pixel from a first image is separately identified. In other embodiments, a group of or all locations and the associated pattern are tracked together to identify a subsequent displaced group of or all locations. Based on the tracked flow, the movement and the display time between each sequential or between two different images is tracked. Spatial locations representing where the flow has moved to in a subsequent image are identified.

In act 36, display values are assigned to the identified spatial locations as a function of the display values from a previous image. The pattern of subsequent images is generated to represent movement of a previous pattern. Perceptually, a pattern from a previous image is shifted to a different position as a function of the direction and magnitude of the flow. The amount and direction of shift indicates the magnitude and direction, respectively, of the flow between two images or over time. Since the later occurring pattern includes information from the earlier occurring pattern, flow is perceived. This stream generation provides a sense of the velocity field as function of the display time. The synthetic pattern or a variation is moved as a function of the display time. The stream or subsequent pattern is represented by:

$$p(x,y,\xi) = p(x+v(x,y,t)d\xi, y+v(x,y,t)d\xi, \xi-d\xi) \quad \text{Eq. 1}$$

where $d\xi$ is the increment of display time. The displayed image, $D(x, y, \xi)$ is provided as follows:

$$D(x, y, \xi) = \begin{cases} s(x, y, t), & v(x, y, t) = 0 \\ p(x, y, \xi), & \text{otherwise,} \end{cases} \quad \text{Eq. 2}$$

where the velocity=0 as a function of acquisition time, the B-mode value s(x, y, t) is displayed. Otherwise, the pattern is displayed as a function of the display time. As a result, flow is shown from image to image as a function of the display time.

The display or pixel values for the later occurring image are based on the pixel values from the pattern generated for the earlier image. The same gray scale, color, hue, brightness and combinations thereof for each tracked pixel are used. The display value may vary as a function of any additional modulation, such as B-mode or color flow mode modulation. The display value may be modulated by a further desired alteration of the pattern for that or each pixel. Rather than using the entire display value, a component of the display value associated with the pattern from the previous image is assigned as a component to the display value in a different location of a subsequent image.

Where two or more pixel locations from a previous image are tracked to a same pixel location in a subsequent image, the two display values from the previous image are averaged, a minimum is selected, a maximum is selected or the display values are combined in some other function. Where a spatial location in the subsequent image is associated with flow but no display value (e.g., pixel component) from a previous image is tracked to the subsequent spatial location, the same pattern as was used previously is used to generate the display value. Alternatively, the display value is assigned as a function of adjacent display values. For example, the variance associated with the subsequent spatial location is used to assign an amount of difference from adjacent spatial locations. Where the flow is from one direction towards another direction, such as from left to right, the pixels associated with the beginning of the flow on the image, such as on the left-hand side of the image, may not have previously generated patterns tracked to those spatial locations. As a result, the spatial locations are either assigned without reference to the previous flow representation and associated pattern, the same pattern is repeated as was used before, or a new pattern is provided for those spatial locations.

The pattern for each subsequent image is responsive to a pattern of a previous image shifted in the flow directions by the magnitudes of the pixels. The pattern may also vary as a function of variance in the flow or other alterations of the pattern to account for static or dynamic changes. Where one or more patterns associated with a plurality of locations are shifted in whole, any portions of the pattern falling outside of locations associated with flow are discarded.

Figure 5A:
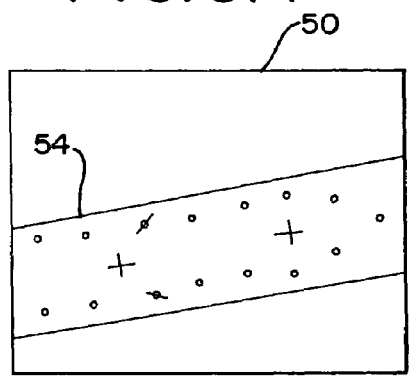
FIGS. 5A and 5B show a pattern persisted across two different images in one embodiment.
Figure 5B:
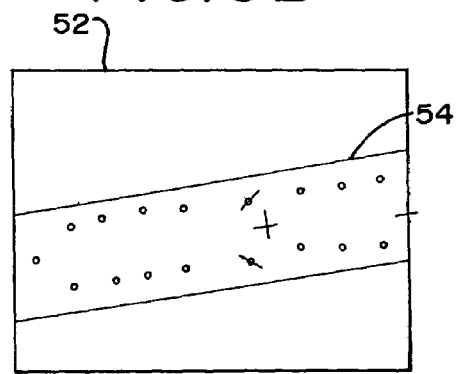

FIGS. 5A and 5B show one example of generating a perceptual stream by persisting a pattern shifted as a function of the flow. The image 52 of FIG. 5B is displayed subsequent to the image 50. The image 52 includes a vessel 54 with a pattern generated for areas associated with flow within the vessel 54. As shown in FIGS. 5A and 5B, the pattern is graphically represented by dots, slashes and plus signs. While such patterns may be used, the pattern is used herein for ease of description. By viewing either of FIG. 5A or 5B alone, the pattern provides little flow information. Alternatively, the pattern varies as a function of flow parameters within a single image. When viewed in sequence, the patterns show a shift associated with flow. For example, the individual slashes and dots at the edges of the vessel 54 are shown to shift by approximately two grid points. Linear shifts, shifts of individual pixels, shifts of groups of pixels or other shift groupings may be used. The center of the vessel associated with more rapid flow shows an increased shift of about three grid points. For example, the plus sign on the left side of the slashes in FIG. 5A is on the right side of the slashes in FIG. 5B after a shift to the right by both the slashes and pluses.

While the entire area associated with flow is provided with a pattern in FIGS. 5A and 5B, alternative embodiments include a pattern for only a portion of the spatial locations associated with flow. For example, a circular, oblong, square, or other regular or irregular shape area associated with flow but less than all areas associated with flow is identified. The pattern is generated for the identified area or the area is the pattern. The pattern is then shifted as discussed herein as a function of display time. For example, FIG. 3 shows a circular area shifting between the images 38 and 40. While the area is shifted, the pattern within the area may also shift. The shape of the area is maintained or is altered as a function of the different pixel shifts.

In one embodiment, the display values for subsequent images are assigned as a weighted combination of display values generated using the previous pattern and a new pattern function. Variation is added to the pattern as a function of time in this embodiment. Using the stream generation discussed above for Equation 1, the locations associated with flow are saturated by the pattern. Additional variation may appear more acceptable or pleasing to a user. For example, two different or even the same pattern generation functions are used. Three or more pattern functions may be used in alternative embodiments. In one embodiment, the pattern for any particular display time at any x, y spatial location is provided by:

$$p(x,y,\xi)=\lambda n(x,y,\xi)+(1-\lambda)p(x+v(x,y,t)d\xi, y+v(x,y,t)d\xi, \xi-d\xi)$$ Eq 3 where $\lambda$ is a small real number between 0 and 1 and $n(x, y, \xi)$ is a different or same pattern generation function as p. $\lambda$ is selected to be between 0 and 1 for implementing an infinite impulse response blending of the two patterns. In one embodiment, $\lambda$ is selected to be small, such as less than 0.1, to more greatly persist the pattern from previous images. In one embodiment, $\lambda$ varies as a function of the variance of flow associated with a single spatial location, group of locations or all locations associated with flow. For example, $\lambda$ varies as a function of the variance for the particular x, y spatial location having display values assigned. Both the pattern functions n and p assign the same component of the display value, such as the gray scale or color. Alternatively, the components alter different components of the display values, such as p assigning a gray scale and n for assigning a color. By varying $\lambda$ as a function of the variance, changes in the scan plane result in a more different pattern. By changing the scan plane, a variance is increased. An increase in variance provides an increase in $\lambda$. The increase in $\lambda$ value results in a more heavy weighting of the newer pattern information n. In alternative embodiments, the pattern n is a function of previous patterns. A finite impulse response or other combinations of the new pattern and the persisted previous pattern may be used.

In one embodiment, the display values for locations associated with flow are controlled only as a function of the pattern or patterns. Alternatively, a same or different component of the display values is responsive to other information, such as coloring, shade, hue or brightness as a function of flow velocity, acceleration or tissue elasticity. In yet another embodiment, B-mode or intensity information associated with moving or stationary tissue is used to also modulate the display values. This modulation addresses the least significant bits (LSBs) of the B-mode or intensity information in one embodiment, having no effect on bits exceeding the threshold for a tissue/flow decision. For example, the gray scale component of the display values is modulated or controlled as a function of both the pattern and the intensity information. Since the intensity information is substantially stationary or slowly moving, the pattern associated with the intensity values shifts less or not at all as compared with the pattern associated with flow. This combination is mathematically represented by:

$$D(x,y,\xi)=\hat{s}(x,y,t)+\alpha p(x,y,\xi)$$

$$(D(x,y,z,\xi)=\hat{s}(x,y,z,t)+\alpha p(x,y,z,\xi) \text{ in 4-D})$$ Eq. 4 where $\hat{s}(x,y,t)$ is the portion of $s(x,y,t)$ that exceeds the tissue/flow threshold. I.e., $s(x, y, t)=\hat{s}(x, y, t)+\check{s}(x, y, t)$, where $\check{s}(x,y,t)$ is the portion of $s(x, y, t)$ that is less than the tissue/flow threshold. In alternate embodiments, Eq. 4 is replaced with:

$$D(x, y, \xi) = \begin{cases} s(x, y, t), & |v(x, y, t)| < \varepsilon \\ \alpha\, s(x, y, t) + (1-\alpha)p(x, y, \xi), & \text{otherwise,} \end{cases}$$ Eq. 4' where $\varepsilon$ is a small velocity threshold and $0 \alpha \leq 1$. In alternative embodiments, $\hat{s}(x,y,t)$ and $p(x,y,\xi)$ are coded into two distinct segments of the display pixel value to generate a transparent effect. The display pixel value consisting of N bits, the low M bits are coded with the $\hat{s}(x,y,t)$, and the high N-M bits are coded with $p(x,y,\xi)$, or the other way around. Look-up tables are used to generate a different colored transparent display effect. In yet other alternative embodiments, the maximum B-mode intensity or the maximum intensity over a region or time is used to set thresholds for motion that is appealing to the viewer. The maximum can be computed over a sequence of images and require processing over two stages (non real-time), or computed over previous images in the sequence and persisted with greater or less dependence on the current image processed In one embodiment, the pattern representing flow modulates a color, such as using different shades or brightnesses of blue and the B-mode information modulates a gray scale. The pattern associated with flow will appear to be blue or liquid while the B-mode information is displayed as a shade of gray. In alternative embodiments, the flow information is a modulated red, yellow or orange color. Different colors may be used. Where the display values are modulated as a function of velocity, the velocity value may be angle corrected to account for components of motion parallel with the face of the transducer.

Rate of change information or flow is displayed in a two- or three-dimensional image using a synthetic motion or a synthetic stream pattern. A display for viewing the change of a parameter, such as a pattern responsive to flow, over time is provided. The rate of change of the parameter is proportional to the perceived motion of the pixel over time.

While the invention has been described above by reference to various embodiments, it should be understood that many changes and modifications can be made without departing from the scope of the invention. For example, the pattern used to represent flow is a speckle pattern identified from image information or correlated to the echo magnitude. Any pattern or grouping of display values that persist some information from one image to a next may be used to show flow over time rather than or in addition to instantaneous flow viewable on only a single image.

What is claimed is:

1. A method for representing flow with a medical imaging system, the method comprising using the medical imaging system to perform the steps of:
   (a) assigning first display values to each of a first plurality of spatial locations of a first image;
   (b) tracking a flow direction and magnitude for each of the first plurality of spatial locations;
   (c) identifying a second plurality of spatial locations as a function of the flow directions and magnitudes, the second plurality of spatial locations corresponding to locations in a second image; and
   (d) assigning second display values of the second image to each of the second plurality of spatial locations as a function of the first display values of the first image such that the second display values have a perceived similarity to the first display values but shifted spatially between the first and second images.

2. The method of claim 1 wherein (a) comprises generating a first pattern for the first plurality of spatial locations for a first image, the first plurality of spatial locations associated with flow, and (d) comprises generating a second pattern for the second plurality of spatial locations for a second image, the second plurality of spatial locations associated with flow, each of the second plurality of spatial locations of the second pattern responsive to the first pattern shifted by the flow direction and magnitude for each of first plurality of spatial locations.

3. The method of claim 1 wherein (a) comprises assigning as a function of a random field with a normal distribution.

4. The method of claim 1 wherein (a) and (d) comprise assigning at least one characteristic of the first and second display values as modulated gray scale values, color, hue or combinations thereof.

5. The method of claim 4 further comprising:
   (e) modulating the first and second display values also as a function of B-mode signals, color flow signals, or combinations thereof.

6. The method of claim 1 wherein (d) comprises assigning the second display values as a weighted combination of the first display values and a pattern function.

7. A method for representing flow with a medical imaging system, the method comprising using the medical imaging system to perform the steps of:
   (a) generating a first pattern for a plurality of pixels associated with flow for a first image;
   (b) determining a spatial offset between the first image and a second image as a function of the flow;
   (c) generating a second pattern for the pixels associated with flow for the second image, the second pattern determined as a function of the first pattern, the second pattern being positioned in the second image as a function of the spatial offset; and
   (d) determining a flow direction and magnitude for each of the plurality of pixels;
   wherein (c) comprises generating the second pattern as a function of the flow direction and magnitude.

8. The method of claim 7 wherein (a) comprises generating the first pattern with a normal distribution with a width of the distribution being a function of a variance of flow.

9. The method of claim 7 wherein (a) comprises modulating gray scale values of pixel display values for the plurality of pixels.

10. The method of claim 9 further comprising:
    (d) modulating a color of the pixel display values for the plurality of pixels as a function of a flow characteristic.

11. The method of claim 9 further comprising:
    (d) modulating the gray scale pixel display values also as a function of B-mode signals for the plurality of pixels.

12. The method of claim 7 wherein (c) comprises generating the second pattern as representing movement of the first pattern.

13. The method of claim 7 wherein (a) and (c) comprise indicating a direction of flow with a shift of the first pattern to a different position, the second pattern including information from the shifted first pattern.

14. The method of claim 7 wherein (a) and (c) comprise indicating a magnitude of flow with a shift of the first pattern to a different position, the second pattern including information from the shifted first pattern.

15. A system for representing flow in medical imaging, the system comprising:
    a processor operable to generate an at least partially persistent pattern in each of at least two images representing a region of a patient, the persistent pattern shifted, in a second of the images as compared to a first of the images, as a function of flow direction, flow magnitude or combinations thereof in the first of the images, the processor operable to calculate a second pattern in the second of the images as a function of a first pattern in the first of images; and
    a display operable to display the at least two images;
    wherein the processor is operable to assign the first pattern to each of a first plurality of spatial locations in the first of the at least two images, to track a flow direction and magnitude for each of the first plurality of spatial locations, to identify a second plurality of spatial locations as a function of the flow direction and magnitude, and to assign second display values to each of the second plurality of spatial locations in the second of the at least two images as a function of the first display values.

* * * * *